United States Patent
Boehm, Jr. et al.

(10) Patent No.: US 6,692,515 B2
(45) Date of Patent: Feb. 17, 2004

(54) SURGICAL KIT FOR REPAIRING LEAKS IN FLUID CARRYING VESSELS AND ORGANS AND METHOD THEREOF

(76) Inventors: Frank H. Boehm, Jr., 2408 Genesee St., Utica, NY (US) 13501; Benedetta Delorenzo Melnick, 1406 Schuyler St., Rome, NY (US) 13440

( * ) Notice: Subject to any disclaimer, the term of this patent is extended or adjusted under 35 U.S.C. 154(b) by 4 days.

(21) Appl. No.: 10/056,841

(22) Filed: Nov. 7, 2001

(65) Prior Publication Data

US 2003/0085148 A1 May 8, 2003

(51) Int. Cl.$^7$ .............................................. A61B 17/08
(52) U.S. Cl. ........................................................ 606/213
(58) Field of Search ........................................ 606/213

(56) References Cited

U.S. PATENT DOCUMENTS

| | | | |
|---|---|---|---|
| 5,649,959 A | * | 7/1997 | Hannam et al. ............ 606/213 |
| 5,773,418 A | * | 6/1998 | Edwardson et al. ........... 514/21 |
| 5,951,589 A | * | 9/1999 | Epstein et al. ............... 606/213 |
| 6,045,570 A | * | 4/2000 | Epstein et al. ............... 606/214 |
| 6,056,769 A | * | 5/2000 | Epstein et al. ............... 606/213 |
| 6,183,498 B1 | * | 2/2001 | Devore et al. ............... 606/214 |
| 6,371,975 B2 | * | 4/2002 | Cruise et al. ................ 606/214 |

* cited by examiner

Primary Examiner—Gary Jackson
(74) Attorney, Agent, or Firm—Dilworth & Barrese, LLP

(57) ABSTRACT

A surgical kit for percutaneously repairing post-operative leaks in internal fluid carrying vessels and organs. The kit includes at least one syringe and at least one marker for placement on the body of the patient to mark the location of the leak. The syringe and marker are enclosed in a sterile package which includes a top cover and a bottom cover. A method for repairing a leak in a fluid carrying vessel or organ, such as the dura mater of the spinal cord, is also disclosed.

3 Claims, 5 Drawing Sheets

SURGICAL KIT FOR REPAIRING LEAKS IN FLUID CARRYING VESSELS AND ORGANS AND METHOD THEREOF

BACKGROUND OF THE INVENTION

1. Field of the Invention

The present invention relates to a surgical kit for repairing leaks in fluid carrying vessels and organs, and in particular, to a surgical kit for percutaneously repairing post-operative cerebrospinal fluid leaks associated with intraoperative rents of the dura mater of the spinal cord.

2. Description of the Related Art

Surgical procedures involving fluid carrying vessels and organs have risks associated with them that can extend beyond the actual surgery itself. Once the actual surgery is complete, the patient must be closely monitored to ensure that leaks at the surgical site do not develop. With the advent of many popular minimally invasive surgical procedures, such as laparoscopy, the vast benefits associated with the minimally invasive procedure may be lost if the patient must return to the operating room to close leaks that develop in fluid carrying vessels, particularly if the leak must be closed using traditional open surgical techniques.

Post-operative leaks are of particular concern following neurosurgical procedures. The human spine is comprised of the spinal column, having many vertebra which support the body and protect the delicate spinal cord. The vertebra are generally of pentagon shape, with the spinal processes (or "points") extending posteriorly to the patient's back. The vertebra are separated and cushioned from each other by the discs, which act as pads between the vertebra to permit movement and shock absorption for the spine. The center of the vertebra are hollow, to permit the spinal cord to extend from the base of the spine to join with the medulla oblongata of the brain. Nerves extend outwardly from the spinal cord between the vertebra. The brain and the spinal cord itself are covered with three main layers: the pia mater, the arachnoid membrane, and the dura mater. The pia mater is a generally thin vascular membrane which is covered by the arachnoid membrane. The arachnoid membrane is in turn covered by the dura mater, which is a tough fibrous membrane that contains and provides a passageway for the cerebrospinal fluid (CSF) to flow. Following neurosurgery, the patient is closely monitored to determine if a rent in the dura mater has developed, which can have deleterious effects on the patient.

In the prior art, once a dural rent is identified, it is common to place a spinal drain at the site and the patient is placed in the Trendelenburg position, with his head positioned below the feet at about a 30–40 degree angle, with the knees bent. Typically, this will solve the problem; however, if the leak is not sealed, oftentimes surgery is necessary to close the rent and prevent further leakage of the CSF. This of course is traumatic to the recovering patient.

A need, therefore, exists for a kit having the instruments required for performing percutaneous procedures to repair leaks in fluid carrying vessels and organs without requiring the patient to undergo a traditional surgical procedure to repair the vessel or organ. A minimally invasive surgical technique is also needed to repair fluid leaks, such CSF leaks in the spinal cord, that may be accomplished quickly and efficiently, to reduce the recovery time of the patient and to minimize the trauma associated with such repair procedures.

SUMMARY OF THE INVENTION

It is, therefore, an object of the present invention to provide a surgical kit to facilitate the percutaneous repair of leaks in internal fluid carrying vessels and organs.

It is also an object of the present invention to provide a surgical kit for repairing post-operative CSF leaks in the dura mater following neurosurgery in a minimally invasive manner.

It is yet another object of the present invention to provide a minimally invasive method for repairing leaks in internal fluid carrying vessels and organs, particularly CSF leaks in the dura mater of the spinal cord.

The above and other objects are achieved by providing a surgical kit for repairing leaks in fluid carrying vessels and organs which includes a syringe and at least one marker in a sterile package, the syringe for containing fibrin glue for sealing the leak and the at least one marker for placement on the body of the patient to mark the location of the leak. In a preferred embodiment, the kit includes the syringe and at least one marker, and a package for containing the syringe and marker, where the package includes a top cover and a bottom cover for enclosing the syringe and marker. In another embodiment, the kit includes a syringe, a container carrying a bio-compatible fluid such as a fibrin glue, at least one marker, and a package having a top cover and a bottom cover for containing the syringe, container and marker. In another embodiment, the kit includes a syringe filled with a fluid such as a fibrin glue for sealing the leak, at least one marker, and a package including a top cover and a bottom cover for containing the syringe and marker. Preferably, the marker is adhesive-backed for maintaining its placement location on the body of the patient, and includes a hole in its center through which the needle of the syringe may pass, to guide the needle to the location of the leak. In addition, it is preferred that the syringe have calibrations or graduations on outer surface to enable the physician to gauge the depth of penetration of the needle to ensure accurate placement of the needle with respect to the leak site. The kit may also be provided with other items that will assist in the repair procedure, such as a container, or even a second syringe, containing a contrast agent to facilitate locating the leak under radiographic or magnetic imaging, such as fluoroscopy, CT scan and magnetic resonance imaging (MRI). A dual chamber syringe, a dual lumen needle attached to the syringe, and even two syringes each carrying the separate components of the fibrin glue are also contemplated. Sterile surgical drapes may also be included.

A method for repairing leaks in internal fluid carrying vessels and organs is also provided, which is minimally invasive and includes the steps of determining the location of the leak, placing a marker on the patient's body to mark the location of the leak, providing a syringe and a fibrin glue material, inserting the needle through a guide hole in the marker into the patient's body to a location adjacent the leak, and delivering the fibrin glue to seal the leak. It is contemplated that the method be performed under radiographic or magnetic imaging to confirm the accuracy of the location of the leak, the accuracy of the placement of the marker and the needle with respect to the leak site, and the accuracy of the delivery of the fibrin glue.

BRIEF DESCRIPTION OF THE DRAWINGS

The above and other objects, features and advantages of the present invention will become more readily apparent from the following detailed description of the preferred embodiments, taken in conjunction with the accompanying drawings, in which.

DETAILED DESCRIPTION OF THE PREFERRED EMBODIMENTS

Figure 1:
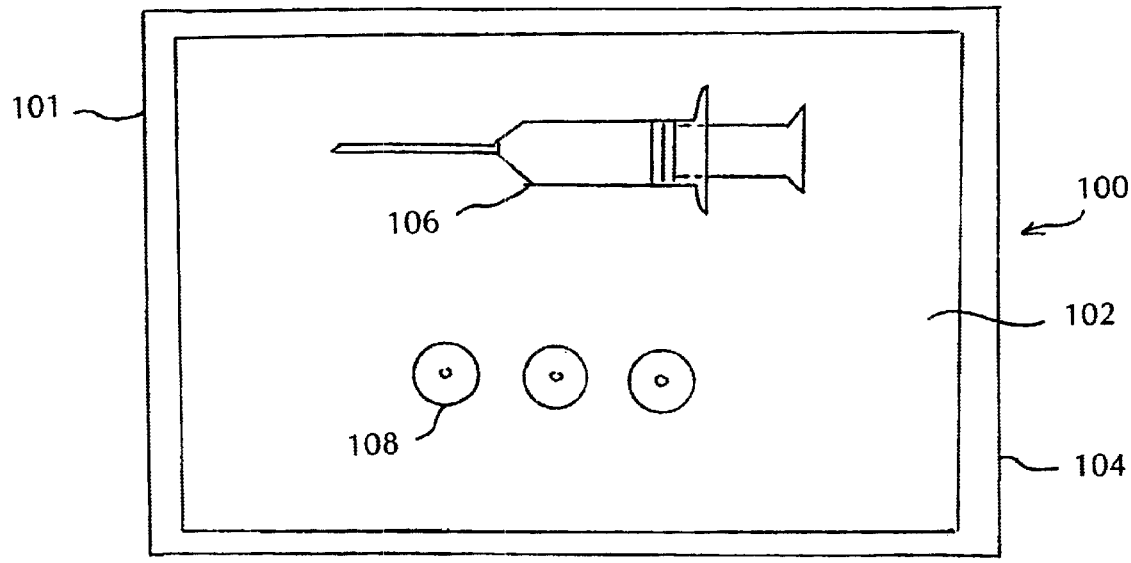
FIG. 1 illustrates a surgical kit for repairing leaks in fluid carrying vessels and organs according to a first embodiment of the present invention.
Figure 8:
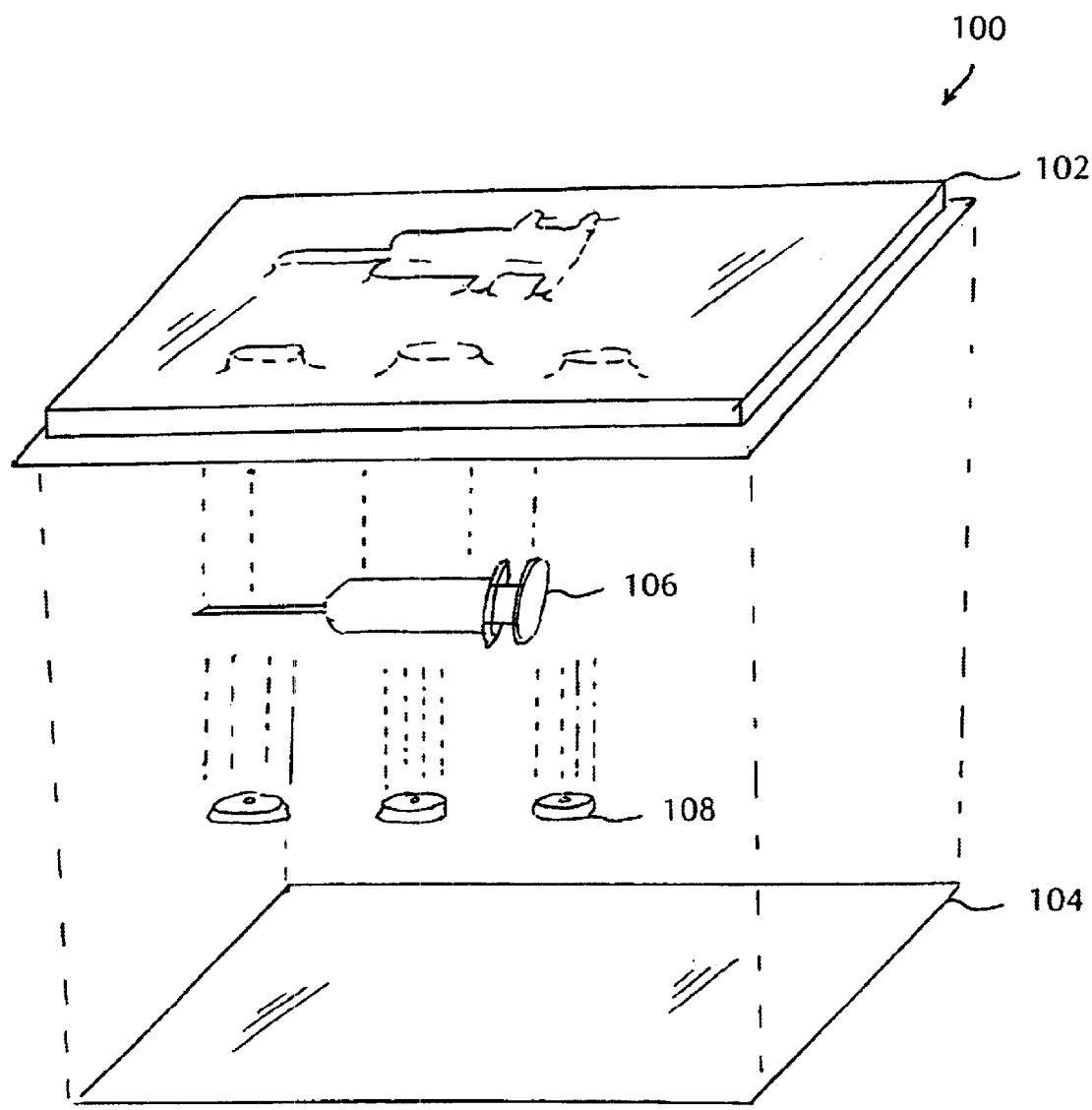
FIG. 8 illustrates an exploded perspective view of the surgical kit of FIG. 1.

Referring now to the drawings, in which like reference numerals identify similar or identical elements throughout the several views, and in particular to FIG. 1, there is shown a surgical kit 100 for repairing leaks in fluid carrying vessels and organs according to the present invention. Surgical kit 100 includes a syringe 106 and a plurality of markers 108 for use in repairing leaks in internal vessels and organs, as will be described below. Syringe 106 preferably includes markings or graduations on its needle, to assist the physician in locating the distal tip of the needle with respect to the leak site inside the patient's body. The syringe 106 may be pre-filled with a bio-compatible fibrin glue material for delivery to the breach or rent in the wall of the vessel or organ, or may be provided empty for filling by the physician during the repair procedure. Referring also to FIG. 8, the kit 100 includes package 101, which consists of top cover 102 and bottom cover 104, which enclose and house the syringe 106 and the plurality of markers 108. Preferably, top cover 102 is a molded plastic cover, with spaces for the syringe and markers to hold them in place and to facilitate assembly. Bottom cover 104 preferably overlays top cover 102 and is secured thereto by heat sealing or other known methods. The entire package is preferably sterilized.

Figure 2:
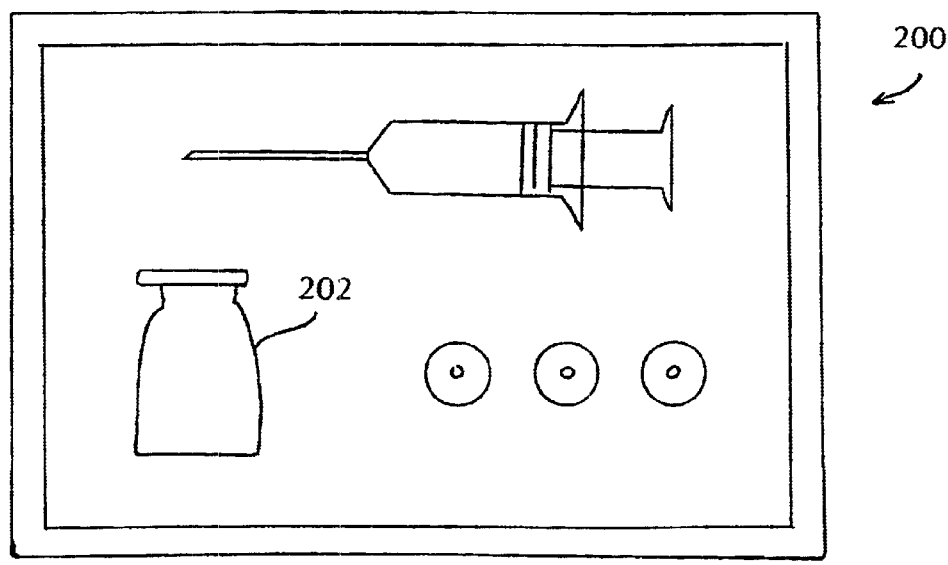
FIG. 2 illustrates a second embodiment of the surgical kit of the present invention.

FIG. 2 illustrates another embodiment of the surgical kit of the present invention. Kit 200 is similar to kit 100 except for the addition of container 202 to the package. Container 202 contains a glue material for delivery to the leak site to seal the leak. In use, the physician removes the syringe 106 and container 202 from the package, and fills the syringe with the glue by drawing the glue into the syringe in a known manner for delivery to the leak site. Alternatively, the container may contain one of the components of a fibrin glue, while the syringe is filled with an equal amount of the other component. Fibrin glue is typically equal parts fibrin and platelets.

Figure 3:
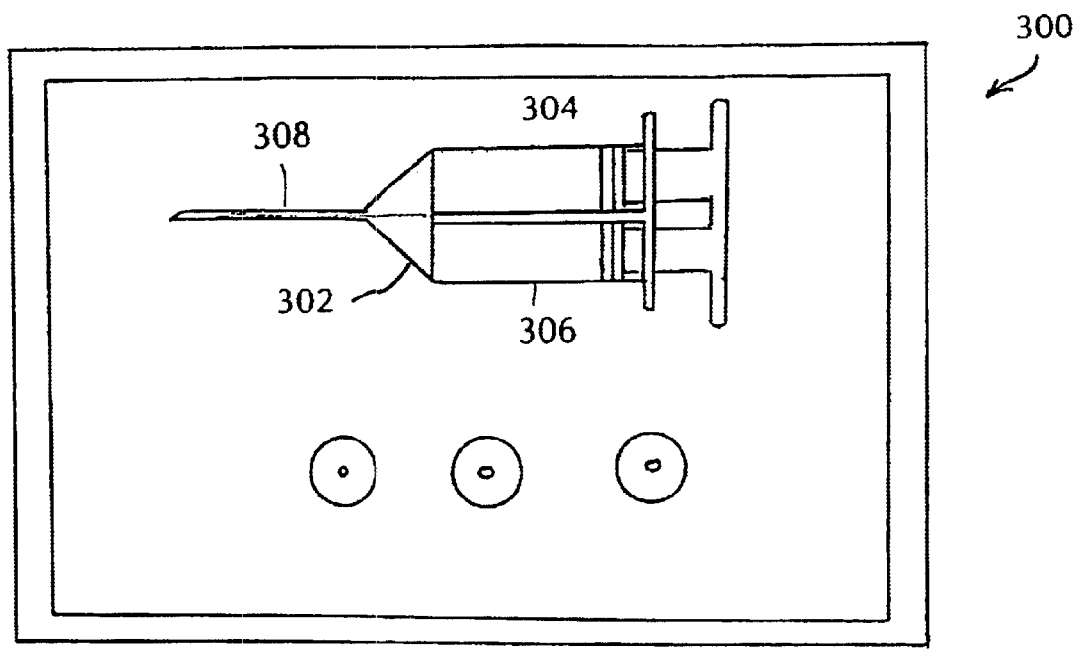
FIG. 3 illustrates a third embodiment of the surgical kit of the present invention.

FIG. 3 illustrates a preferred embodiment of the kit of the present invention. Kit 300 is similar to kit 100 except that dual chamber syringe 302 replaces single chamber syringe 106 of kit 100. Syringe 302 includes chambers 304 and 306, and contains the fluid components of a fibrin glue, which gel and harden upon contact with each other when mixed together. Chamber 304 may contain fibrin, while chamber 306 may contain an equal amount of platelets. The dual chambers prevent the glue material from gelling until the fluids are delivered to the leak site. The dual chamber syringe 302 is preferably constructed with a dual lumen needle 308 attached thereto, which maintains the contents of chamber 304 separate from the contents of chamber 306 until the fluids are adjacent the tip 310 of needle 308, so that the components of the fibrin glue do not mix until they are very close to the leak site.

Figure 4:
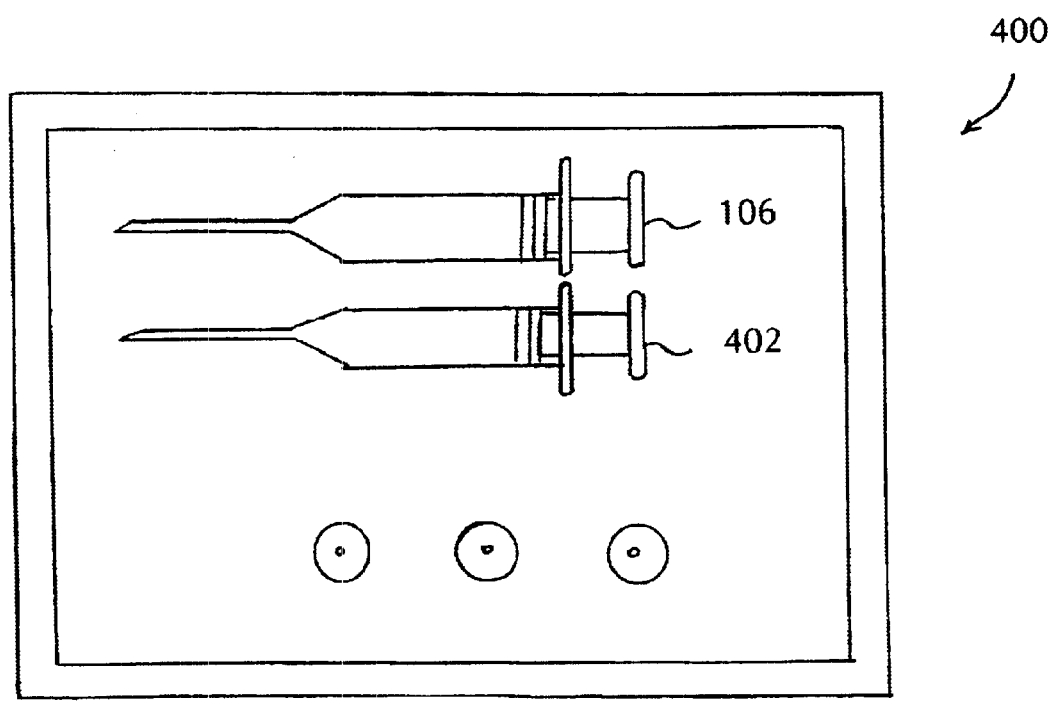
FIG. 4 illustrates a fourth embodiment of the surgical kit of the present invention.
Figure 5:
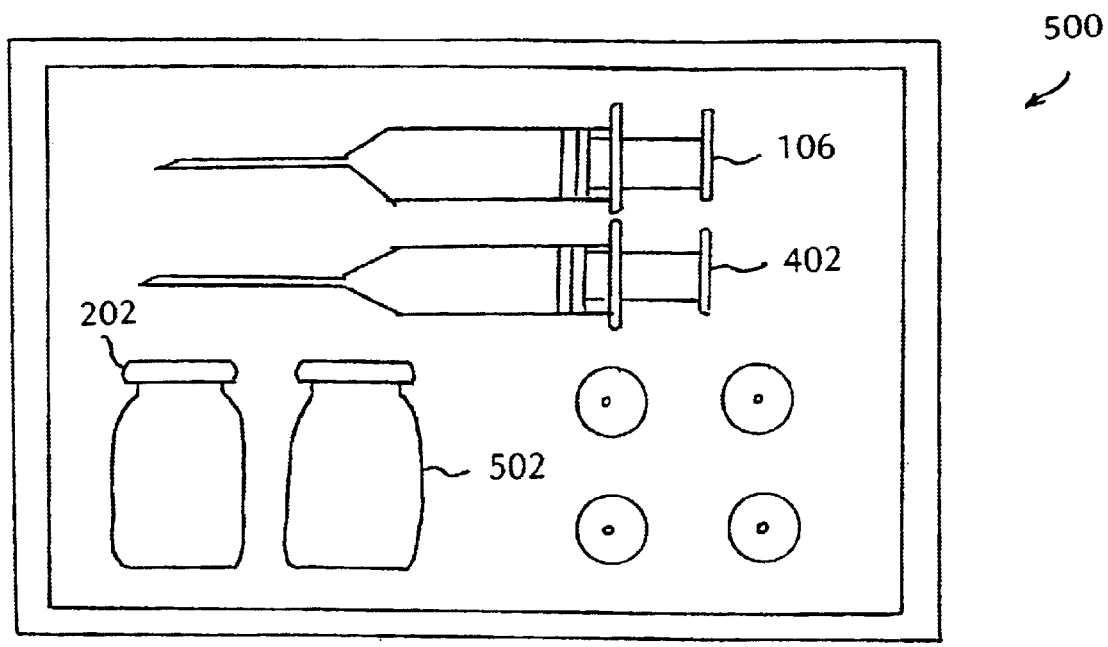
FIG. 5 illustrates a fifth embodiment of the surgical kit of the present invention.

FIG. 4 illustrates yet another embodiment of the kit of the present invention. Kit 400 is similar to kit 100 except for the addition of a second syringe 402, which is provided preferably for the delivery of a contrast agent for intrathecal injection into the spinal cord in the patient's body when the kit 400 is used in procedures to repair leaks in the dura mater of the spinal cord following a neurosurgical procedure, to assist in determining the location of the leak. The contrast agent is preferably a radiographic agent, such as a myelographic contrast agent, but of course can be any contrast agent that is sensitive to scanning techniques such as fluoroscopy, CT scanning, MRI, and the like. The contrast agent can be provided in a pre-filled syringe 402, or may be provided separately during the repair procedure. Alternatively, the contrast agent may be provided in a kit having a container 502 filled with the contrast agent, along with syringe 402, syringe 106 and container 202 filled with the fibrin glue material, all provided in a package 500 as shown in FIG. 5.

Figure 6:
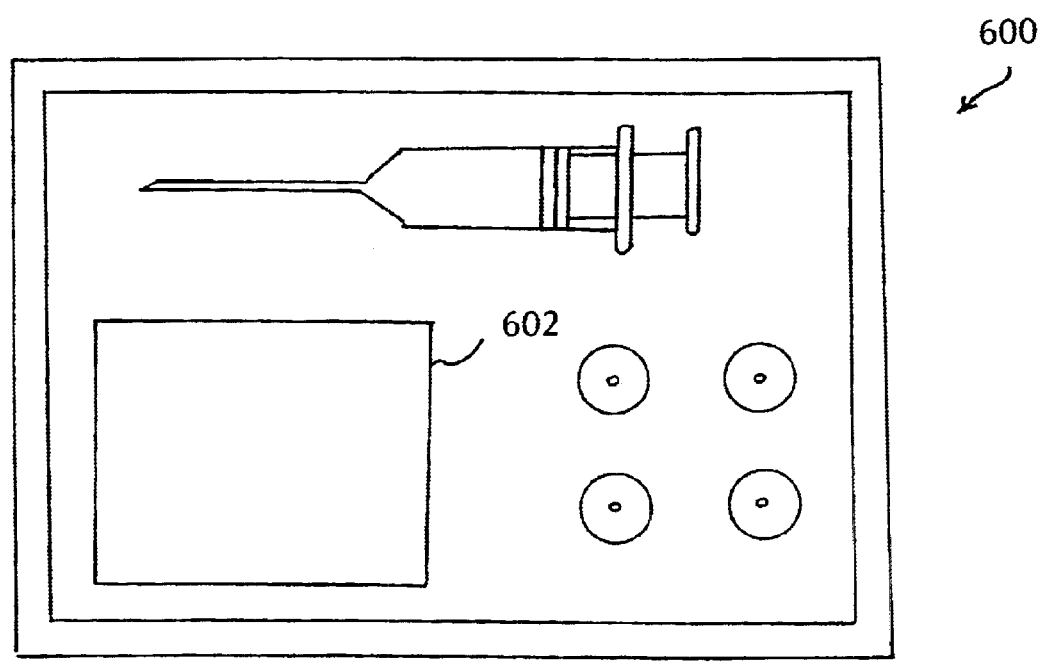
FIG. 6 illustrates a sixth embodiment of the surgical kit of the present invention.

FIG. 6 illustrates a further embodiment of the kit of the present intention. Kit 600 is similar to kit 100 except for the addition of surgical drape 602, which can be used during the surgical repair procedure.

Figure 7:
FIG. 7 illustrates a marker of the present invention, for placement on the patient's body to mark the location of the leak in a fluid carrying vessel or organ.

FIG. 7 illustrates a preferred embodiment of the fiducial marker 108 that is packaged with the kit of the present invention, and used in accordance with the method of repairing a leak in a fluid carrying vessel or organ of the present invention. Preferably, the marker 108 is constructed of a radiopaque plastic material and includes a centrally located hole 710, which is of a size that can accommodate the needle of syringe 106. The marker 108 is adhesive backed for securement to the skin of the patient.

Figure 9:
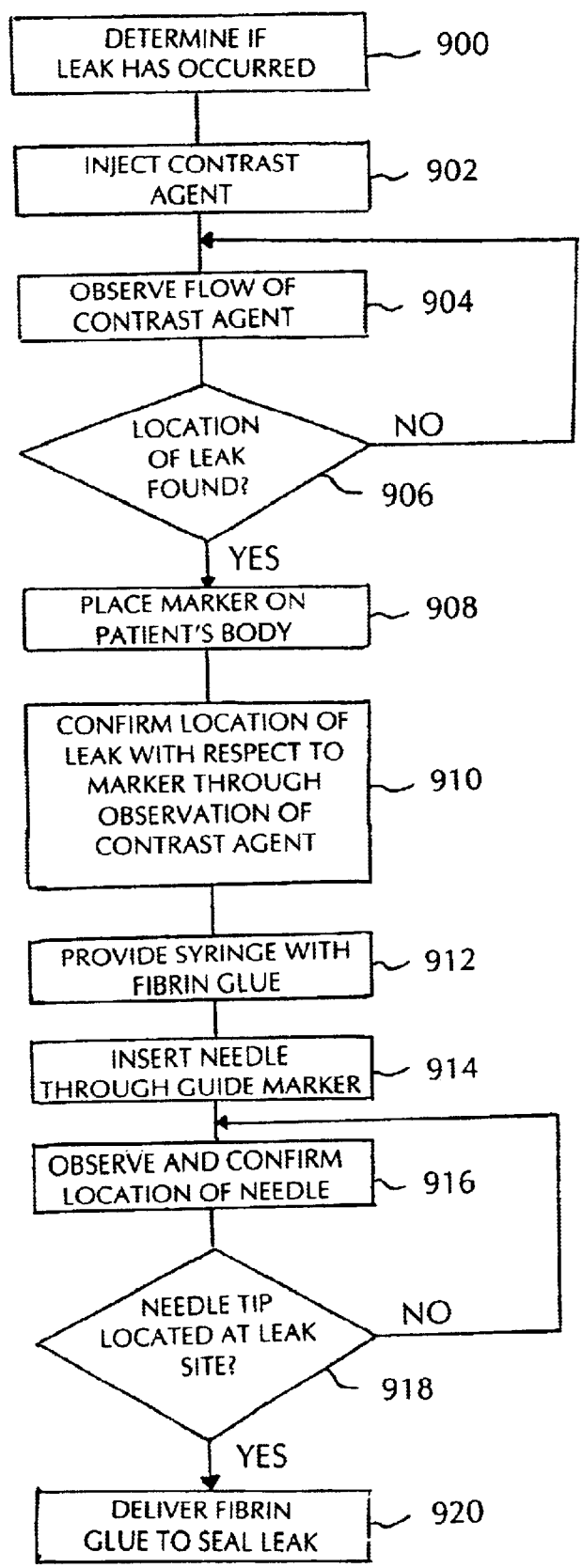
FIG. 9 is a flow chart of the method of repairing a leak in fluid carrying vessels and organs of the present invention.

FIG. 9 is a flowchart setting forth the method of the present invention, which utilizes the kit of the present invention. In step 900, it is determined that a patient is suffering from a post-operative rent or leak in a fluid carrying vessel organ. The present invention is particularly suited for the repair of post-operative CSF leaks, following neurosurgical procedures, where the rent has occurred in the dura mater of the spinal cord. Pinhole-sized leaks in the dura mater usually will seal themselves, while the patient is maintained in the Trendelenburg position until the rent is sealed. However, in the event the rent does not seal itself, after the leak is discovered in step 900, the patient is injected with a radiographic contrast agent intrathecally at step 902, and the flow of the contrast agent is observed at step 904 under CT, MRI, fluoroscopy, or the like. If the location of the leak is determined at step 906, a marker, such as marker 108 of kit 100 described above, is affixed to the patient's body in step 908. If the leak site is not located to the satisfaction of the physician, the process returns to step 904.

Once the marker is placed, its location is confirmed with respect to the leak site through continued scanning at step 910. A syringe, such as syringe 106 of kit 100 or syringe 302 of kit 300, is then provided containing a fibrin glue material at step 912. The needle of the syringe is inserted into the patient's body through the guide hole 710 of marker 108 at step 914. The tip of the needle is positioned adjacent the rent, and its position is observed and confirmed by observation of the graduations on the needle of the syringe and through continued scanning at step 916. Once it is determined at step 918 that the tip of the needle is located at the site of the leak, the fibrin glue is delivered to seal the leak at step 920. If it is determined that the needle is not properly positioned, the process returns to step 916.

While the invention has been shown and described with reference to certain preferred embodiments, it will be understood by those skilled in the art that various changes in form and detail may be made therein without departing from the spirit and scope of the invention, as defined by the appended claims.

What is claimed is:

1. A method for repairing a fluid leak in internal fluid carrying vessels and organs, comprising the steps of:

determining that a leak has occurred in a fluid carrying vessel or organ;

injecting a radiographic contrast agent into the fluid carrying vessel or organ;

observing flow of the contrast agent using radiographic imaging to determine the location of the leak;

placing a marker on the patient's body to mark the location of the leak;

confirming the location of the leak with respect to the marker using radiographic imaging;

providing a syringe having a needle and containing a fibrin glue material;

inserting the needle into the patient's body through the marker;

confirming the location of the distal tip of the needle of the syringe using radiographic imaging; and delivering the fibrin glue material to the location of the leak to seal the leak on the fluid carrying vessel or organ.

2. A method for repairing a CSF leak in the dura mater of the spinal cord, comprising the steps of:

(a) determining that a leak has occurred;

(b) determining the location of the leak;

(c) placing a marker on the patient's body to mark the location of the leak;

(d) providing a syringe having a needle and containing fibrin glue;

(e) inserting the needle into the patient's body through the marker to the location of the leak; and (f) delivering the fibrin glue to the location of the leak to seal the leak in the dura mater.

3. The method of claim 2, further comprising the step of delivering a contrast agent to the dura mater and observing at least steps (b), (c), (e) and (f) through scanning techniques.

* * * * *